(12) United States Patent
Park Choo et al.

(10) Patent No.: US 8,614,240 B2
(45) Date of Patent: Dec. 24, 2013

(54) BENZOXAZOLE DERIVATIVES HAVING INHIBITORY ACTIVITY AGAINST INTERLEUKIN-6, PREPARATION METHOD THEREOF, AND PHARMACEUTICAL COMPOSITION CONTAINING THE SAME

(75) Inventors: Hea Young Park Choo, Seoul (KR); Young Kook Kim, Daejeon (KR); Jung Ho Choi, Daejeon (KR); Jin Ah Kim, Gyeonggi-do (KR)

(73) Assignee: EWHA University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 13/805,136

(22) PCT Filed: Jun. 17, 2011

(86) PCT No.: PCT/KR2011/004436
§ 371 (c)(1),
(2), (4) Date: Dec. 18, 2012

(87) PCT Pub. No.: WO2011/159124
PCT Pub. Date: Dec. 22, 2011

(65) Prior Publication Data
US 2013/0090480 A1    Apr. 11, 2013

(30) Foreign Application Priority Data

Jun. 18, 2010 (KR) .................. 10-2010-0057844

(51) Int. Cl.
*A61K 31/423*    (2006.01)
*C07D 271/12*    (2006.01)

(52) U.S. Cl.
USPC ........................................ 514/375; 548/222

(58) Field of Classification Search
None
See application file for complete search history.

(56) References Cited

U.S. PATENT DOCUMENTS 7,531,553 B2    5/2009    Di Pietro et al.

FOREIGN PATENT DOCUMENTS

WO        9842377        10/1998
WO        2004085425 A1  10/2004

OTHER PUBLICATIONS

"Alzheimer's disease." CNN Health, Obtained Oct. 9, 2010, URL:http://www.cnn.com/2003/HEALTH/conditions/09/24/alzheimers.drug.ap/index.html.*

Antonio R. Damasio, Alzheimer's Disease and Related Dementias, Cecil Textbook of Medicine, 20th edition (1996), vol. 2, pp. 1992-1996.*
Enomoto, A.; Rho, M. C.; Fukami, A.; Hiraku, O.; Komiyama, K.; Hayashi, M., Suppression of cancer cachexia by 20S,21-epoxyresibufogenin-3-acetate—a novel nonpeptide IL-6 receptor antagonist. Biochem Biophys Res Commun 2004, 323 (3), 1096-102.
Nishimoto, N., Clinical studies in patients with Castleman's disease, Crohn's disease, and rheumatoid arthritis in Japan. Clin Rev Allergy Immunol 2005, 28 (3), 221-30.
Hirano, T.; Yasukawa, K.; Harada, H.; Taga, T.; Watanabe, Y.; Matsuda, T.; Kashiwamura, S.; Nakajima, K.; Koyama, K.; Iwamatsu, A.; et al., Complementary DNA for a novel human interleukin (BSF-2) that induces B lymphocytes to produce immunoglobulin, Nov. 6, 1986.
Norihino Nishimoto et al., "Study of active controlled monotherapy used for rheumatoid arthritis, an IL-6 inhibitor (SAMURAI): evidende of clinical and radiographic benefit from an X-ray reader-blinded randomised controlled trial of tocilizumab", Ann Rheum Dis, 2007, 66, pp. 1162-1167.
Lindmark, E.; Diderholm, E.; Wallentin, L.; Siegbahn, A., Relationship between interleukin 6 and mortality in patients with unstable coronary artery disease: effects of an early invasive or noninvasive strategy. JAMA 2001, 286 (17), 2107-13.
Taga, T.; Kawanishi, Y.; Hardy, R. R.; Hirano, T.; Kishimoto, T., Receptors for B cell stimulatory factor 2. Quantitation, specificity, distribution, and regulation of their expression. J Exp Med 1987, 166 (4), 967-81.
Kang, B. S.; Chung, E. Y.; Yun, Y. P.; Lee, M. K.; Lee, Y. R.; Lee, K. S.; Min, K. R.; Kim, Y., Inhibitory effects of anti-inflammatory drugs on interleukin-6 bioactivity. Biol Pharm Bull 2001, 24 (6), 701-3.
Jones, S. A.; Horiuchi, S.; Topley, N.; Yamamoto, N.; Fuller, G. M., The soluble interleukin 6 receptor: mechanisms of production and implications in disease. FASEB J 2001, 15 (1), 43-58.
Heinrich, P. C.; Behrmann, I.; Muller-Newen, G.; Schaper, F.; Graeve, L., Interleukin-6-type cytokine signalling through the gp130/Jak/STAT pathway. Biochem J 1998, 334 (Pt 2), 297-314.
Heinrich, P. C.; Behrmann, I.; Haan, S.; Hermanns, H. M.; Muller-Newen, G.;Schaper, F., Principles of interleukin (IL)-6-type cytokine signalling and its regulation. Biochem J 2003, 374 (Pt 1), 1-20.
Hayashi, M.; Rho, M. C.; Enomoto, A.; Fukami, A.; Kim, Y. P.; Kikuchi, Y.; Sunazuka, T.; Hirose, T.; Komiyama, K.; Omura, S., Suppression of bone resorption by madindoline A, a novel nonpeptide antagonist to gp130. Proc Natl Acad Sci USA 2002, 99 (23), 14728-33.

* cited by examiner

*Primary Examiner* — Alicia L Otton
(74) *Attorney, Agent, or Firm* — Benjamin Aaron Adler

(57) ABSTRACT

The present invention relates to benzoxazole derivatives represented by the Formula 1, which has an inhibitory activity against interleukin-6 (IL-6), a method for preparation thereof, and a pharmaceutical composition containing the same. The compound represented by the Formula 1 according to the present invention has a superior inhibitory activity against interleukin-6, and therefore, can be practically applied for prevention and treatment of diseases caused by abnormal interleukin-6 activity.

13 Claims, 5 Drawing Sheets

Antibody: p44/42 (cellsignaling 9106), secondary antibody: Rabbit

US 8,614,240 B2

BENZOXAZOLE DERIVATIVES HAVING INHIBITORY ACTIVITY AGAINST INTERLEUKIN-6, PREPARATION METHOD THEREOF, AND PHARMACEUTICAL COMPOSITION CONTAINING THE SAME

TECHNICAL FIELD

The present invention relates to novel benzoxazole derivatives having inhibitory activity against interleukin-6 (IL-6), a method for preparation thereof, and a pharmaceutical composition containing the same.

BACKGROUND ART

Interleukin-6 (IL-6) is a cytokine known as stimulating B cell factor or known as interferon-$\beta 2$, which is a non-glycosylated polypeptide chain comprised of 185 amino acids. IL-6 was discovered as a differentiation factor involved in the activation of B lymphocytic cells (Hirano, T.; Yasukawa, K.; Harada, H.; Taga, T.; Watanabe, Y.; Matsuda, T.; Kashiwamura, S.; Nakajima, K.; Koyama, K.; Iwamatsu, A.; et al., Complementary DNA for a novel human interleukin (BSF-2) that induces B lymphocytes to produce immunoglobulin. *Nature* 1986, 324 (6092), 73-6), and then identified as a multifunctional cytokine which affects differentiation and proliferation of T cells, differentiation of nerve cells, formation of osteoclast, production of acute phase protein in hepatocyte, etc. (Akira, S.; Taga, T.; Kishimoto, T., Interleukin-6 in biology and medicine. *Adv Immunol* 1993, 54, 1-78). In addition, IL-6 is secreted from various cells including T cell and macrophage, and plays a role in maintaining the homeostasis of living bodies by inducing on immune reaction and inhibiting TNF-$\alpha$, IL-1, etc., and further regulates the expression of a specific gene in the liver when an acute phase immune reaction occurs and controls the survival of normal plasmablastic cells (Ishihara, K.; Hirano, T., IL-6 in autoimmune disease and chronic inflammatory proliferative disease. *Cytokine Growth Factor Rev* 2002, 13 (4-5), 357-68).

Meanwhile, it has been reported that IL-6 reduces insulin sensitivity, and thus is also involved in the induction of insulin-resistant diabetes; induces blood coagulation by promoting secretion of cellular adhesion factors and secretion of fibrinogen in hepatic tissues; increases cholesterol synthesis or decreases secretion of cholesterol; and induces arteriosclerosis through upregulation of Lecithin cholesterol acyltransferase (LCAT) and apolipoprotein A-1 (apo A-1) genes (Omoigui, S., Cholesterol synthesis is the trigger and isoprenoid dependent interleukin-6 mediated inflammation is the common causative factor and therapeutic target for atherosclerotic vascular disease and age-related disorders including osteoporosis and type 2 diabetes. *Med Hypotheses* 2005, 65 (3), 559-69; Yudkin, J. S.; Kumari, M.; Humphries, S. E.; Mohamed-Ali, V., Inflammation, obesity, stress and coronary heart disease: is interleukin-6 the link? *Atherosclerosis* 2000, 148 (2), 209-14). Further, it has also been reported as the result of research that in cases where the concentration of IL-6 involved in inflammation formation increases, the risk of an onset of heart diseases and the fatality rate thereof are increased. Diseases caused by the increase of the production of IL-6 include Alzheimer disease, rheumatoid arthritis, inflammation, myocardial infarction, Paget's disease, osteoporosis, solid tumors (RCC), bladder cancer, prostate cancer, Castleman syndrome, etc. (Ishihara, K.; Hirano, T., IL-6 in autoimmune disease and chronic inflammatory proliferative disease. *Cytokine Growth Factor Rev* 2002, 13 (4-5), 357-68; Lindmark, E.; Diderholm, E.; Wallentin, L.; Siegbahn, A., Relationship between interleukin 6 and mortality in patients with unstable coronary artery disease: effects of an early invasive or noninvasive strategy. *JAMA* 2001, 286 (17), 2107-13).

Recently, the number of patients suffering from inflammation-related diseases induced by abnormal IL-6 activity, including rheumatoid arthritis, Castleman syndrome, Crohn's disease, osteoporosis, cancer cachexia, arteriosclerosis, diabetes, etc. is rapidly tending upwards. Although research to develop an agent for treatment of metabolic diseases represented by rheumatoid arthritis, osteoporosis, arteriosclerosis and diabetes has been made worldwide, the development of an agent for treatment thereof has been unsatisfactory so far. IL-6 has recently came under interest as an important factor for inflammatory reaction deeply related to the onset and progress of such metabolic diseases.

Meanwhile, interleukin 6 receptor (IL-6R) has been known as a type I cytokine receptor called Cluster of Differentiation 126 (CD126), and transmits its biological activities through the medium of 2 kinds of cellular proteins. Respective proteins are comprised of polypeptide chains of $\alpha$-subunit and $\beta$-subunit. $\alpha$-Subunit is a ligand binding chain having the molecular weight of about 80 kDa, and is designated as gp80 or CD126. It is present in the form of soluble IL-6 R mainly comprised of its extracellular domain, as well as in the form of a membrane-binding form, which penetrates the cell membrane and is expressed in the cell membrane. $\beta$-Subunit is gp130 or CD130, and has been known as having the molecular weight of 130 kDa. It is a membrane-binding protein and takes part in signal transduction (Taga, T.; Kawanishi, Y.; Hardy, R. R.; Hirano, T.; Kishimoto, T., Receptors for B cell stimulatory factor 2. Quantitation, specificity, distribution, and regulation of their expression. *J Exp Med* 1987, 166 (4), 967-81).

In addition, it is a domain commonly contained in cytokine family such as oncostatin M (OSM), leukemia inhibitory factor (LIF), IL-11, cardiotrophin-1 (CT-1), and ciliary neurotrophic factor (CNTF), and is found in most living organs including the heart, kidney, spleen, liver, lung, placenta, brain, etc. (Kang, B. S.; Chung, E. Y.; Yun, Y. P.; Lee, M. K.; Lee, Y. R.; Lee, K. S.; Min, K. R.; Kim, Y., Inhibitory effects of anti-inflammatory drugs on interleukin-6 bioactivity. *Biol Pharm Bull* 2001, 24 (6), 701-3; Jones, S. A.; Horiuchi, S.; Topley, N.; Yamamoto, N.; Fuller, G. M., The soluble interleukin 6 receptor: mechanisms of production and implications in disease. *FASEB J* 2001, 15 (1), 43-58). Further, IL-6 and IL-6R form the IL-6/IL-6R complex, which is then bound to gp130, thereby transmitting the biological activities of IL-6 into cells.

In 1994, a signal transduction system utilizing Jak family, tyrosine kinase, and STAT family, a transcription factor, as the main mediators for signal transduction was discovered. Various cytokines including IL-6, and IFNs and growth factors have signal transduction system mechanism in common. Upon initiation of the stimulation Jak1, Jak2, and Tyk2 as gp130-associated kinase are activated, and the cytoplasmic tail of gp130 is phosphorylated. Phosphotyrosine residues of gp-130 is a docking site, which is mainly paired with SH2 domains of STAT3 and STAT1. Then, STAT is phosphorylated and forms a dimer, which is then migrated into a nucleus to regulate the transcription of the target gene (Heinrich, P. C.; Behrmann, I.; Muller-Newen, G.; Schaper, F.; Graeve, L., Interleukin-6-type cytokine signalling through the gp130/Jak/STAT pathway. *Biochem J* 1998, 334 (Pt 2), 297-314).

Ras-Raf pathway allows the binding of tyrosine phosphatase SHP2 to phosphorylated gp130, and allows the connection with mitogen-activated protein kinase (MAPK) pathway. Finally, NF-IL-6 (a C/EBP family member) and AP-1 (c-Jun, c-Fos) as the transcription factor are activated to cause the biological reaction. It has been expected that a series of MAPK pathway related to Ras signal transduction IL-6 plays an important role in cell differentiation and proliferation.

Research to reveal the role of IL-6 in a series of signal transduction systems induced by IL-6 more in more detail is in progress, and thus the exact information on respective steps is being revealed. According to this, the complexity of inflammatory reaction is being amplified, and more minor new target procedures for the respective diseases are being derived therefrom. Therefore, if IL-6 inhibitors are developed as the target of the signal transduction system induced by IL-6, it helps to identify the mechanism of the signal transduction system, and at the same time, enables the development of medical products.

In the study of IL-6 activity inhibitors related thereto, antibody against IL-6 (anti-IL-6 antibody), antibody against IL-6R (anti-IL-6 receptor antibody) and antibody against gp130 (anti-gp130 antibody), IL-6 modification, IL-6 or IL-6R partial peptides, etc. have been reported (Heinrich, P. C.; Behrmann, I.; Haan, S.; Hermanns, H. M.; Muller-Newen, G.; Schaper, F., Principles of interleukin (IL)-6-type cytokine signalling and its regulation. *Biochem J* 2003, 374 (Pt 1), 1-20; Novick, D.; Engelmann, H.; Revel, M.; Leitner, O.; Rubinstein, M., Monoclonal antibodies to the soluble human IL-6 receptor: affinity purification, ELISA, and inhibition of ligand binding. *Hybridoma* 1991, 10 (1), 137-46; Huang, Y. W.; Vitetta, E. S., A monoclonal anti-human IL-6 receptor antibody inhibits the proliferation of human myeloma cells. *Hybridoma* 1993, 12 (5), 621-30; Mihara, M, Preventives or remedies for sensitized T cell-related diseases containing IL-6 antagonists as the active ingredient. WO9842377, 1998).

Particularly, it has been reported that tocilizumab as a IL-6R neutralizing antibody (MRA) alleviates the symptoms of patients suffering from Castleman syndrome, Crohn's disease and rheumatoid arthritis [Nishimoto, N., Clinical studies in patients with Castleman's disease, Crohn's disease, and rheumatoid arthritis in Japan. *Clin Rev Allergy Immunol* 2005, 28 (3), 221-30).

Madindoline A developed as an IL-6 activity inhibitor by the Kitasato Institute of Japan is a non-cytotoxic indole alkaloid separated from the fermentation culture solution of *Streptomyces nitrosporeus* K930711, and forms a non-covalent bond competitively with the extracellular domain of gp130 (Structural Formula 1). This compound inhibits the formation of osteoclasts induced by IL-6 through the inhibition of the homodimerization of gp130 to inhibit JAK/STAT signal transduction procedures, and has an effect of alleviating the symptoms of osteoporosis in menopause-induced mice. However, madindoline A has the disadvantages that it is difficult to synthesize in a mass scale due to complex synthetic procedures, and the production from microorganisms is also of an extremely minor yield (Hayashi, M.; Rho, M. C.; Enomoto, A.; Fukami, A.; Kim, Y. P.; Kikuchi, Y.; Sunazuka, T.; Hirose, T.; Komiyama, K.; Omura, S., Suppression of bone resorption by madindoline A, a novel nonpeptide antagonist to gp130. *Proc Natl Acad Sci USA* 2002, 99 (23), 14728-33).

As other IL-6R inhibitor, A20S,21-epoxy-resibufogenin-3-formate (ERBF) is a material discovered through screening of natural substances, and was separated from bufadienolide.

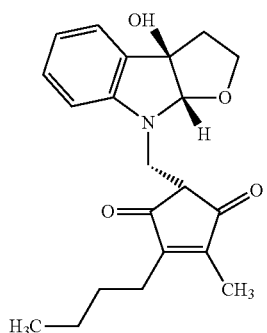

Madindoline A

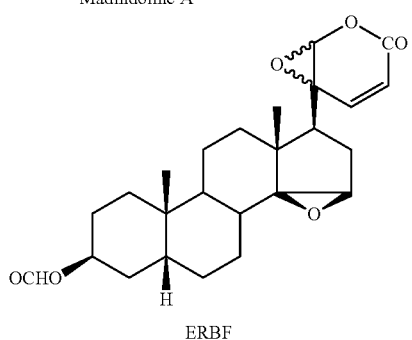

ERBF

It inhibits cancer cachexia induced by Colon-26. However, since the total synthetic method for the preparation of ERBF has not yet been developed, ERBF also has the disadvantage that its production through separation from natural substances is extremely limited (Enomoto, A.; Rho, M. C.; Fukami, A.; Hiraku, O.; Komiyama, K.; Hayashi, M., Suppression of cancer cachexia by 20S,21-epoxy-resibufogenin-3-acetate-a novel nonpeptide IL-6 receptor antagonist. *Biochem Biophys Res Commun* 2004, 323 (3), 1096-102).

As described above, although basic research of various diseases, which can be induced by abnormal IL-6 activity has been ongoing, much of their attack mechanisms have not yet been clearly defined, and thus the study of various vital phenomena caused by the inhibition of IL-6 activity is incomplete.

That seems to be caused by the poor progress of the development of low molecular materials, which specifically inhibit the activity of IL-6. Therefore, if low molecular compounds, which can be synthesized on a large scale and specifically inhibit the activity of IL-6, could be developed, it is considered that the relationship between IL-6 and related diseases will be more exactly defined, and the compounds thus developed can be utilized for the development of medical products. Thus, the present inventor has identified that novel benzoxazole derivatives can satisfy such requirements, thereby completing the present invention.

DISCLOSURE

Technical Problem

The purpose of the present invention is to provide novel benzoxazole derivatives as a low molecular compound useful as an interleukin-6 activity inhibitor.

In addition, the purpose of the present invention is to provide a method for the preparation of a novel benzoxazole derivative.

The purpose of the present invention is further to provide a pharmaceutical composition which comprises a novel benzoxazole derivative or a pharmaceutically acceptable salt thereof for prevention or treatment of diseases or symptoms caused by abnormal interleukin-6 activity.

Further, the purpose of the present invention is to provide a method for preventing or treating diseases or symptoms caused by abnormal interleukin-6 activity, which comprises the step of administering to a subject as needed a pharmaceutical composition comprising novel benzoxazole derivatives or a pharmaceutically acceptable salt thereof.

Another purpose of the present invention is to provide a pharmaceutical composition comprising a novel benzoxazole derivative or a pharmaceutically acceptable salt thereof for use in prevention or treatment of diseases or symptoms caused by abnormal interleukin-6 activity.

Still another purpose of the present invention is to provide a use for a pharmaceutical composition comprising novel benzoxazole derivatives or a pharmaceutically acceptable salt thereof for use in the preparation of a medicine for prevention or treatment of diseases or symptoms caused by abnormal interleukin-6 activity.

Technical Solution

To attain said purposes the present invention provides a compound represented by the following Formula 1:

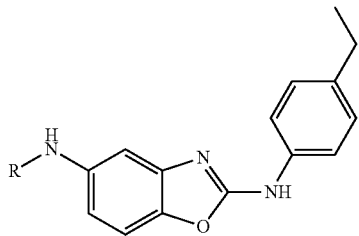

Formula 1 or a pharmaceutically acceptable salt thereof, wherein
R is hydrogen, $R_1CH_2CO$ or $R_1CO$,
$R_1$ is phenyl which is unsubstituted or substituted with identical or different one to three substituents, each independently selected from the group consisting of $C_{1-10}$ alkyl; halogen; nitro; $C_{1-4}$ haloalkyl; $C_{1-4}$ alkoxy and

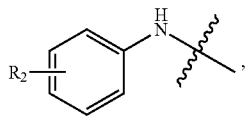

and
$R_2$ is $C_{1-4}$ haloalkyl.

In the above, $R_1$ is preferably phenyl substituted with one $C_{1-10}$ alkyl; $C_{1-4}$ haloalkyl; halogen and

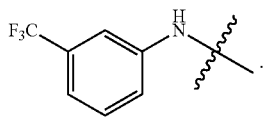

In addition, said $R_1$ is preferably phenyl substituted with identical or different two substitutents each independently selected from the group consisting of halogen; nitro; $C_{1-4}$ haloalkyl and $C_{1-4}$ alkoxy, and more preferably phenyl substituted with halogen and nitro; phenyl substituted with halogen and $C_{1-4}$ haloalkyl; phenyl substituted with two halogens; or phenyl substituted with two $C_{1-4}$ alkoxy.

In addition, said $R_1$ is preferably phenyl substituted with three $C_{1-4}$ alkoxy.

Further, said $R_1$ is preferably phenyl which is unsubstituted or substituted with identical or different one to three substituents each independently selected from the group consisting of ethyl; t-butyl; heptyl; chloromethyl; trifluoromethyl; fluoro; chloro; nitro; methoxy; ethoxy; and

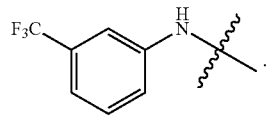

In the above, $R_2$ is preferably trifluoromethyl.

In addition, the compounds represented by the above Formula 1 can be any one selected from the group consisting of the following:
1) $N^2$-(4-ethylphenyl)benzo[d]oxazole-2,5-diamine,
2) N-(2-(4-ethylphenylamino)benzo[d]oxazol-5-yl)-2-phenylacetamide,
3) N-(2-(4-ethylphenylamino)benzo[d]oxazol-5-yl)benzamide,
4) 4-chloro-N-(2-(4-ethylphenylamino)benzo[d]oxazol-5-yl)benzamide,
5) 2-chloro-N-(2-(4-ethylphenylamino)benzo[d]oxazol-5-yl)-4-nitrobenzamide,
6) 2-chloro-N-(2-(4-ethylphenylamino)benzo[d]oxazol-5-yl)-5-nitrobenzamide,
7) 3,4-dichlorobenzamide-N-(2-(4-ethylphenylamino)benzo[d]oxazol-5-yl)-benzamide,
8) 3-(chloromethyl)-N-(2-(4-ethylphenylamino)benzo[d]oxazol-5-yl)-benzamide,
9) 4-ethyl-N-(2-(4-ethylphenylamino)benzo[d]oxazol-5-yl)benzamide,
10) N-(2-(4-ethylphenylamino)benzo[d]oxazol-5-yl)-3-fluoro-5-(tri-fluoromethyl)benzamide,
11) 2-ethoxy-N-(2-(4-ethylphenylamino)benzo[d]oxazol-5-yl)benzamide,
12) 4-t-butyl-N-(2-(4-ethylphenylamino)benzo[d]oxazole-5-yl)benzamide,
13) N-(2-(4-ethylphenylamino)benzo[d]oxazol-5-yl)-3,4-dimethoxybenzamide,
14) N-(2-(4-ethylphenylamino)benzo[d]oxazol-5-yl)-3,4,5-trimethoxybenzamide,
15) N-(2-(4-ethylphenylamino)benzo[d]oxazol-5-yl)-4-heptylbenzamide, and
16) N-(2-(4-ethylphenylamino)benzo[d]oxazol-5-yl)-2-(3-(trifluoro-methyl)phenylamino)benzamide.

In the present invention, the pharmaceutically acceptable salts refer to salts conventionally used in the pharmaceutical industry, and include, for example, salt prepared from inorganic acids including hydrochloric acid, nitric acid, phosphoric acid, hydrobromic acid, hydroiodic acid, perchloric acid, tartaric acid and sulfuric acid, salts prepared from organic acids including methanesulfonic acid, ethanesulfonic acid, benzenesulfonic acid, p-toluenesulfonic acid, naphthalenesulfonic acid, acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid galacturonic acid, glutamic acid, glutaric acid, glucuronic acid, aspartic acid, ascorbic acid, carbonic acid, vanillic acid, hydriodic acid, etc., and salts prepared from amino acids including glycine, arginine, lysine, etc. but the kinds of salts included in the present invention are not limited to the salts listed above. Such pharmaceutically acceptable salts can be prepared by conventional methods, for example, by dissolving the benzoxazole of the present invention in an excessive aqueous solution in which said pharmaceutically acceptable acids are dissolved, and precipitating the salts by means of a water-miscible organic solvent such as methanol, ethanol, acetone or acetonitrile.

In another embodiment, the present invention provides a method for preparation of the compound represented by the above Formula 1, which comprises the step of reacting a compound represented by the following Formula 2:

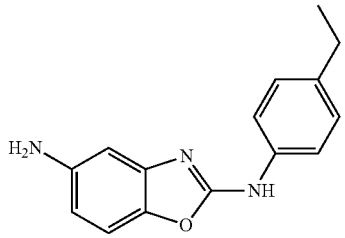

Formula 2 with a compound represented by the following Formula 3:

R—X    Formula 3 in the presence of a base, wherein R is defined as above, but R is not hydrogen.

In the preparation method of the present invention, the compound represented by the above Formula 2 can be a compound prepared by reacting a product obtained from the reaction of 4-nitro-aminophenol and 4-ethylphenylisothiocyanate with potassium peroxide ($KO_2$), and then reducing a nitro group into an amine group (under Pd/C catalyst and hydrogen gas).

In the preparation method of the present invention, the base is preferably tertiary organic bases. For example, the base is preferably one or more selected from triethylamine, N,N-diisopropylethylamine, N-methylmorpholine, N-methylpiperidine, 4-dimethyl aminopyridine, N,N-dimethylaniline, 2,6-lutidine, and pyridine, and is more preferably N,N-diisopropylethylamine.

In the preparation method of the present invention, the equivalent ratio of the compound represented by the above Formula 2 and the compound represented by the above Formula 3 is preferably 1:0.9 to 1.5, and more preferably 1:1 in view of the efficiency of reagents with regard to financial considerations.

In the preparation method of the present invention, the reaction solvent can be those selected from, but not limited to, alcohols such as methanol, ethanol, isopropanol, etc., acetonitrile, chloroform, methylene chloride, tetrahydrofuran, N,N-dimethylformamide, N-methylpyrrolidinone, DMF (dimethylformamide) and the like. Among them, DMF is preferable. The reaction solvent is used preferably in an amount of 1 to 20 ml, more preferably in an amount of 3 to 5 ml, with respect to 1 mmol of the compound represented by the above Formula 2.

In the preparation method of the present invention, the reaction temperature can be in the range between 0° C. and the reflux temperature of the reaction solvent, preferably in the range of 10 to 40° C., and more preferably in the range of room temperature, i.e. 15 to 30° C.

In the preparation method of the present invention, the reaction time can be varied depending on the reaction temperature, the reaction solvent, etc., but is preferably about 2 hours to 48 hours.

In another embodiment, the present invention provides a pharmaceutical composition which comprises the compound represented by the above Formula 1 or a pharmaceutically acceptable salt thereof for prevention or treatment of diseases or symptoms caused by abnormal interleukin-6 activity.

Said diseases or symptoms caused by abnormal interleukin-6 activity can include Alzheimer's disease, rheumatoid arthritis, inflammation, myocardial infarction, Paget's disease, osteoporosis, solid tumors (RCC), bladder cancer, prostate cancer, Castleman disease, Crohn's disease, arteriosclerosis and diabetes.

The pharmaceutical composition of the present invention can further comprise one or more of the known active ingredients having an effect for prevention or treatment of diseases or symptoms caused by abnormal interleukin-6 activity.

The pharmaceutical composition of the present invention can contain additives including pharmaceutically acceptable diluents, binders, disintegrators, lubricants, pH controlling agents, antioxidants, dissolution aids, etc., within a range which does not adversely influence the effect of the present invention.

As the diluents sugar, starch, microcrystalline cellulose, lactose (lactose hydrate), glucose, di-mannitol, alginate, alkaline earth metals, clay, polyethylene glycols, anhydrous calcium hydrogen phosphate, or the mixture thereof can be used; and as binders starch, microcrystalline cellulose, high-dispersible silica, mannitol, saccharose, lactose hydrate, polyethylene glycol, polyvinylpyrrolidone (povidone), polyvinylpyrrolidone copolymers (co-povidone), hypromellose, hydroxypropyl cellulose, natural gums, synthetic gums, co-povidone, gelatin, or the mixture thereof can be used.

As disintegrators, starch or denatured starch including sodium starch glyconate, corn starch, potato starch, pregelatinized starch, etc.; clays including bentonite, montmorillonite, veegum, etc.; celluloses including microcrystalline cellulose, hydroxypropyl cellulose, carboxymethyl cellulose, etc.; algins including sodium alginate, alginic acid, etc.; cross-linked celluloses including croscarmellose sodium, etc.; gums including gur gum, xanthan gum, etc.; cross-linked polymers including cross-linked polyvinyl pyrrolidone (crospovidone), etc.; effervescent materials including sodium bicarbonate, citric acid, etc.; or the mixture thereof can be used.

As lubricants, talc, stearic acid, magnesium stearate, magnesium stearate, calcium stearate, sodium lauryl sulfate, hydrogenated vegetable oil, sodium benzoate, sodium stearyl fumarate, glyceryl behenate, glyceryl monooleate, glyceryl monostearate, glycery palmitostearate, colloidal silicon dioxide, or the mixture thereof can be used.

As the pH controlling agent, an acidifying agent such as acetic acid, adipic acid, ascorbic acid, sodium ascorbate, sodium etherate, malic acid, succinic acid, tartaric acid, fumaric acid, citric acid, basifying agent such as precipitated calcium carbonate, ammonia water, meglumine, sodium carbonate, magnesium oxide, magnesium carbonate, sodium citrate, tribasic calcium phosphate, etc. can be sued.

As antioxidants, dibutyl hydroxyl toluene, butylate hydroxyanisole, tocopherol acetate, tocopherol, propyl gallate, sodium hydrogen sulfite, sodium pyrosulfite, etc. can be used. As the dissolution aids in the first-releasing section of the present invention sodium lauryl sulfate, polyoxyethylene sorbitan fatty acid esters including polysorbate, etc., sodium docusate, poloxamer, etc. can be used.

Further, enteric-soluble macromolecules, water-insoluble polymers, hydrophobic compounds, and hydrophilic macromolecules can be included to prepare the sustained releasing formulation.

Said enteric-soluble macromolecules refer to a macromolecule which is insoluble or stable under the acidic condition below pH 5 and is dissolved or decomposed under a certain pH condition over pH 5, and include, for example, enteric-soluble cellulose derivatives such as hypromellose acetate succinate, hypromellose phthalate (hydroxypropylmethyl cellulose phthalate), hydroxymethylethyl cellulose phthalate, cellulose acetate phthalate, cellulose acetate succinate, cellulose acetate malate, cellulose benzoate phthalate, cellulose propionate phthalate, methyl cellulose phthalate, carboxymethylethyl cellulose, ethylhydroxyethyl cellulose phthalate, and methylhydroxyethyl cellulose; enteric-soluble acrylic acid-based copolymers such as styrene-acrylic acid copolymers, acrylic acid-methylacrylic acid copolymers, acrylic acid-methyl methacrylate copolymers (e.g., Acryl-EZE), butyl acrylate-styrene-acrylic acid copolymers, and methyl acrylate-methacrylic acid-octyl acrylate copolymers; enteric-soluble polymethacrylate copolymers such as poly(methacrylic acid-methyl methacrylate) copolymers (e.g., Eudragit L, Eudragit S, Evonik, Germany), poly(methacrylic acid-ethyl acrylate) copolymers (e.g., Eudragit L100-55); enteric-soluble maleic acid-based copolymers such as vinyl acetate-maleic anhydride copolymers, styrene-maleic anhydride copolymers, styrene-maleic acid monoester copolymers, vinyl methyl ether-maleic anhydride copolymer, ethylene-meleic anhydride copolymers, vinyl butyl ether-maleic anhydride copolymers, acrylonitrile-methyl acrylate-maleic anhydride copolymers, and butyl acrylate-styrene-maleic anhydride copolymers; and enteric-soluble polyvinyl derivatives such as polyvinyl alcohol phthalate, polyvinyl acetalphthalate, polyvinyl butylate phthalate and polyvinylacetacetal phthalate.

Said water-insoluble polymers refer to a pharmaceutically acceptable, water-insoluble macromolecule, which controls the release of a drug. The water-insoluble polymers can include, for example, polyvinyl acetate (e.g., Kollicoat SR30D), water-insoluble polymethacrylate copolymers (e.g., poly(ethyl acrylate-methyl methacrylate) copolymers (e.g., Eudragit NE30D), poly(ethyl acrylate-methyl methacrylate-trimethyl aminoethyl methacrylate) copolymers (e.g., Eudragit RSPO), etc.), ethyl cellulose, cellulose esters, cellulose ethers, cellulose acylate, cellulose diacylate, cellulose triacylate, cellulose acetate, cellulose diacetate and cellulose triacetate, etc.

Said hydrophobic compounds refer to a pharmaceutically acceptable, water-insoluble material, which controls the release of a drug. They can include, for example, fatty acids or fatty acid esters such as glyceryl palmitostearate, glyceryl stearate, glyceryl behenate, cetyl palmitate, glyceryl monooleate and stearic acid; fatty acid alcohols such as cetostearyl alcohol, cetyl alcohol and stearyl alcohol; waxes such as carnauba wax, beeswax, and microcrystalline wax; inorganic materials such as talc, precipitated calcium carbonate, calcium monohydrogen phosphate, zinc oxide, titanium oxide, kaolin, bentonite, montmorillonite and veegum, and the like.

Said hydrophilic macromolecules mean a pharmaceutically acceptable, water-soluble macromolecule, which controls the release of a drug. They can include, for example, sugars such as dextrin, polydextrin, dextran, pectin and pectin derivatives, alginate, polygalacturonic acid, xylan, arabinoxylan, arabinogalactan, starch, hydroxypropyl starch, amylase, and amylopectin; cellulose derivatives such as hypromellose, hydroxypropyl cellulose, hydroxymethyl cellulose, hydroxyethyl cellulose, methylcellulose and sodium carboxymethyl cellulose; gums such as guar gum, locust bean gum, tragacanth, carrageenan, acacia gum, arabic gum, gellan gum, and xanthan gum; proteins such as gelatin, casein, and zein; polyvinyl derivatives such as polyvinyl alcohol, polyvinyl pyrrolidone and polyvinylacetal diethylaminoacetate; hydrophilic polymethacrylate copolymers such as poly (butyl methacrylate-(2-dimethylaminoethyl)methacrylate-methyl methacrylate) copolymers (e.g., Eudragit E100, Evonik, Germany), poly(ethyl acrylate-methyl methacrylate-triethylaminoethyl-methacrylate chloride) copolymers (e.g., Eudragit RL, RS, Evonik, Germany); polyethylene derivatives such as polyethylene glycol and polyethylene oxide; carbomer, and the like.

In addition, the preparation of the present invention can be formulated by selecting and using pharmaceutically acceptable additives, which are various additives selected from coloring agents and flavors. As such formulating method, the methods disclosed in, for example, Remington's Pharmaceutical Science, Mack Publishing Company, Easton Pa., etc. can be utilized.

In the present invention, although the range of the additives is not be limited to the above-mentioned additives, they can be used at an amount in the conventional range by the selection to prepare the formulation.

The pharmaceutical composition according to the present invention can be prepared in the form of oral formulations such as powder, granule, tablet, capsule, suspension, emulsion, syrup and aerosol, external formulations, suppositories or sterile injectable solutions.

Further, the present invention provides a method for alleviating, preventing or treating diseases or symptoms caused by abnormal interleukin-6 activity, including Alzheimer's disease, rheumatoid arthritis, inflammation, myocardial infarction, Paget's disease, osteoporosis, solid tumors (RCC), bladder cancer, prostate cancer, Castleman disease, Crohn's disease, arteriosclerosis and diabetes, which comprises administering to a mammal the compound represented by the Formula 1.

In the present invention, the term "administering" means that the pharmaceutical composition of the present invention is introduced into a patient by any appropriate method. The pharmaceutical composition of the present invention can be administered via any of general routes as long as it can reach the target tissue. Specifically, the administration of the pharmaceutical composition can be accomplished by, but not limited to, oral, intraperitoneal, intravenous, intramuscular, subcutaneous, intradermal, intranasal, intrapulmonary, itrarectal, intraluminal, intraperitoneal and intradural administration.

The pharmaceutical composition of the present invention can be administered once a day or two or more times a day at regular time intervals.

The dose of the compound represented by the Formula 1 or the pharmaceutically acceptable salts thereof according to the present invention is 0.1 to 1000 mg/kg/day, and can be varied depending on disease severity, age, sex, etc. of patients.

In addition, the present invention provides a use of the compound represented by the Formula 1 or the pharmaceutically acceptable salts thereof according to the present invention in preparing the pharmaceutical preparation for alleviating, preventing or treating diseases or symptoms caused by abnormal interleukin-6 activity, including Alzheimer's disease, rheumatoid arthritis, inflammation, myocardial infarction, Paget's disease, osteoporosis, solid tumors (RCC), bladder cancer, prostate cancer, Castleman disease, Cronh's disease, arteriosclerosis and diabetes.

Advantageous Effects

The benzoxazole derivatives of the present invention have a superior inhibitory activity against interleukin-6, and therefore, can be practically applied to prevention and treatment of diseases caused by abnormal interleukin-6 activity.

BEST MODE

Hereinafter, the present invention will be more specifically illustrated by the following Examples and Experiments. These Examples and Experiments are intended only to explain the present invention, and the scope of the present invention is not limited to the following Examples and Experiments.

The reagents and solvents stated in the following illustration were purchased from Aldrich, Alfa Aesar, Acros or TCI unless specifically stated otherwise. $^1$H-NMR data is a value measured by means of Unity 400 (Varian) instrument, and Mass data is a value measured by means of JMS-AX 505wA and JMS-HX/HX 110A or JMS 700 (JEOL) instruments.

A. Synthesis

Various derivatives having the basic structure of benzoxazole were synthesized. As seen in Scheme 1, these derivatives were synthesized by synthesizing the compound of Example 1 starting from 4-nitro-aminophenol, and then reacting amino group of the compound of Example 1 with benzoyl chloride derivatives having various substituents such as phenyl acetyl chloride and 2-(3-(trifluoromethyl)phenylamino)benzoic acid, etc. to synthesize the compounds of Examples 2-16.

Figure 1:
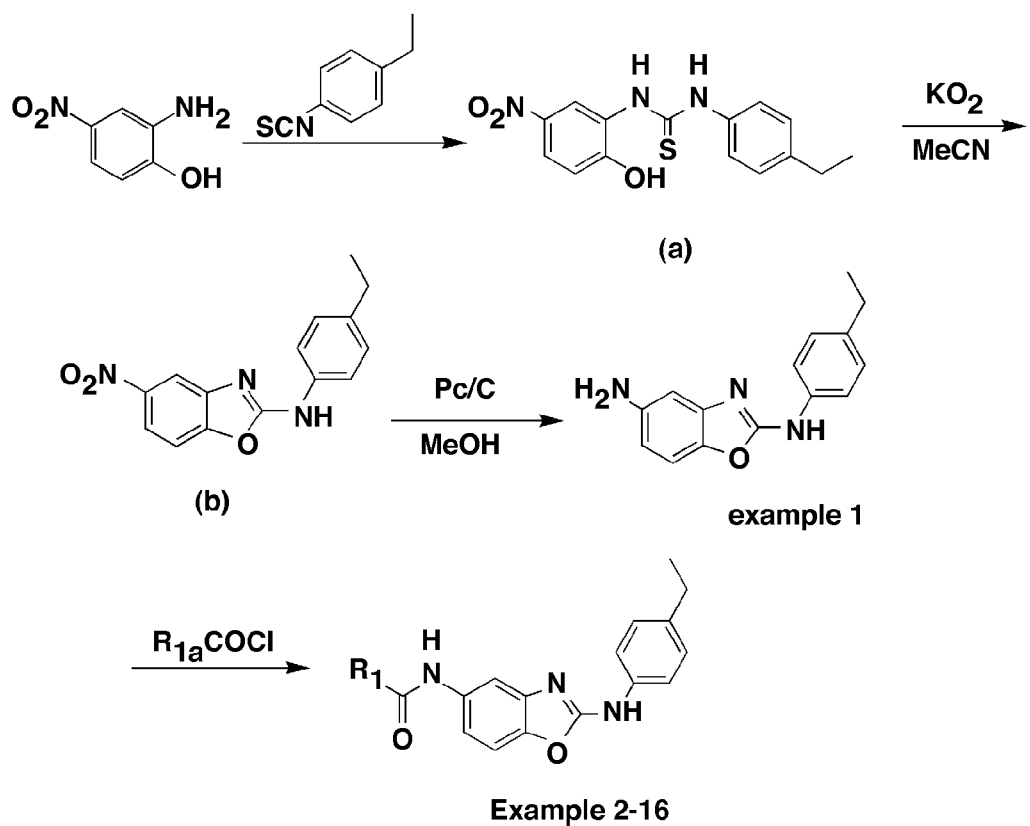
FIG. 1 depicts synthetic scheme 1 for the synthesis of benzoxazole derivatives

(In scheme 1, FIG. 1, $R_{1a}$ is phenyl substituted with identical or different 1 to 3 substituents independently selected from the group consisting of carbonyl group or $C_{1-10}$ alkyl; halogen; nitro; $C_{1-4}$ haloalkyl; $C_{1-4}$ alkoxy and

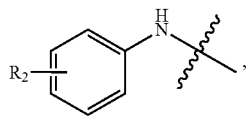

in the definition of substituent R in Formula 1, $R_2$ is $C_{1-4}$ haloalkyl.)

TABLE 1

| Compound | R |
|---|---|
| 1 | H |
| 2 | |
| 3 | |
| 4 | |
| 5 | |
| 6 | |
| 7 | |

TABLE 1-continued

| Compound | R |
|---|---|
| 8 | 3-(chloromethyl)benzoyl |
| 9 | 4-ethylbenzoyl |
| 10 | 3-fluoro-5-(trifluoromethyl)benzoyl |
| 11 | 2-ethoxybenzoyl |
| 12 | 4-tert-butylbenzoyl |
| 13 | 3,4-dimethoxybenzoyl |
| 14 | 3,4,5-trimethoxybenzoyl |
| 15 | 4-heptylbenzoyl (H$_3$C(H$_2$C)$_6$–) |
| 16 | 2-[(3-(trifluoromethyl)phenyl)amino]benzoyl |

Preparation 1

Synthesis of 1-(4-ethylphenyl)-3-(2-hydroxy-5-nitrophenyl)thiourea (a)

4-Ethylphenyl isothiocyanate (3.48 mmol, 1 eq) was added to 2-amino-4-nitrophenol (3.48 mmol, 1 eq) dissolved in 10 mL of methanol, and stirred at room temperature for 24 hours. The organic solvent was removed by evaporation under reduced pressure, and then the precipitate was filtered under reduced pressure with hexane to yield the title compound (a). Yellow-green powder (79%), mp 137-138° C.; $^1$H NMR (Acetone-d$_6$ 400 MHz) δ 9.475 (s, 1H), 9.351 (s, 1H), 8.755 (s, 1H), 7.968 (d, J=9.8 Hz, 1H), 7.464 (d, J=8.0 Hz, 2H), 7.282 (d, J=8.8 Hz, 2H), 7.089 (d, J=9.2 Hz, 1H), 2.658 (q, J=7.6 Hz, 2H), 1.225 (t, J=7.6 Hz, 3H).

Preparation 2

Synthesis of N-(4-ethylphenyl)-5-nitrobenzo[d]-oxazol-2-amine (b)

In an ice bath under nitrogen gas, 15 mL of acetonitrile was slowly added to KO$_2$ (12.05 mmol, 5 eq) with stirring. Then, the compound (a) synthesized in Example 1 (2.41 mmol, 1 eq) in 20 mL of acetonitrile was slowly added to said solution containing KO$_2$. The mixture was reacted at room temperature for 16 hours, and then the reaction solution was diluted with 30 mL of ice water. This solution was extracted with dichloromethane, and washed two times with saturated aqueous NaCl solution. After drying with anhydrous MgSO$_4$, the precipitate obtained by removing the solvent under reduced pressure was filtered under reduced pressure with EtOAc:hexane=1:10 (V/V) to yield the title compound (b). Yellow powder (88%), mp 172-173° C.; $^1$H NMR (Acetone-d$_6$, 400 MHz) δ 9.805 (s, 1H), 8.229 (s, 1H), 8.109 (d, J=8.8 Hz, 1H), 7.764 (d, J=8.4 Hz, 2H), 7.615 (d, J=9.2 Hz, 1H), 7.278 (d, J=8.8 Hz, 2H), 2.651 (q, J=7.6 Hz, 2H), 1.230 (t, J=7.6 Hz, 3H).

Example 1

Synthesis of $N^2$-(4-ethylphenyl)benzo[d]oxazole-2,5-diamine (1)

20 mL of methanol was slowly added dropwise to the compound (b) prepared in Preparation 2 (1.31 mmol, 1 eq) and 5% Pd/C (0.4 g), and then the reaction mixture was charged with hydrogen and stirred at room temperature for 24 hours.

The reaction solution was filtered through celite, and then the solvent was removed from the filtrate under reduced pressure to yield the title compound (I).

Gray solid (88%), mp 143~145° C.; $^1$H NMR (Acetone-$d_6$, 400 MHz) δ 9.170 (s, 1H), 7.737 (d, J=8.4 Hz, 2H), 7.205 (d, J=8.4 Hz, 2H), 7.036 (d, J=8.8 Hz, 2H), 6.752 (s, 1H), 6.439 (d, J=8.4 Hz, 1H), 4.443 (d, J=10.4 Hz, 1H), 2.615 (q, J=7.6 Hz, 2H), 1.210 (t, J=7.6 Hz, 3H). HR-FABMS Calcd for $C_{15}H_{16}N_3O$ (M$^+$+H): 254.1293. Found: 254.1292.

Example 2

Synthesis of N-(2-(4-ethylphenylamino)benzo[d]oxazol-5-yl)-2-phenylacetamide (2)

The compound 1 prepared in Example 1 (1 mmol, 1 eq) was dissolved with DMF (dimethylformamide, 3 mL), and 2-phenylacetyl chloride (1 mmol, 1 eq) and N,N-diisopropylethylamine (1 mmol, 1 eq) were added together thereto. The mixture was then stirred at room temperature for 16 hours. To the reaction solution was added 10% aqueous HCl solution, and the mixture was extracted with 30 mL of EtOAc. The organic layer was washed with 10% aqueous HCl solution, and then two times with saturated $NaHCO_3$ solution and two times with saturated aqueous NaCl solution. After drying with anhydrous $MgSO_4$ and filtering under reduced pressure, the organic solvent was removed under reduced pressure to prepare the title compound.

White solid (56%), mp>250° C.; $^1$H NMR (CDCl$_3$, 400 MHz) δ 7.506-7.461 (m, 2H), 7.437-7.402 (m, 2H), 7.372-7.332 (m, 2H), 7.235-7.160 (m, 4H), 7.054 (s, 1H), 6.915 (s, 1H), 3.769 (s, 2H), 2.639 (q, J=7.3 Hz, 2H), 1.234 (t, J=7.6 Hz, 3H). HR-FABMS Calcd for $C_{23}H_{23}N_3O_2$ (M$^+$+H): 372.1712. Found: 372.1714.

Example 3

Synthesis of N-(2-(4-ethylphenylamino)benzo[d]oxazol-5-yl)benzamide (3)

The title compound was prepared according to the same method as Example 2, except that benzoyl chloride was used in place of 2-phenylacetyl chloride used in Example 2.

White solid (65%), mp 239-240° C.; $^1$H NMR (CDCl$_3$, 400 MHz) δ 7.906-7.886 (m, 2H), 7.821 (s, 1H), 7.702 (d, J=2.0 Hz, 1H), 7.566-7.544 (m, 1H), 7.526-7.490 (m, 3H), 7.450 (dd, J=3.2 Hz, 1H), 7.307 (d, J=8.4 Hz, 1H), 7.232 (d, J=8.4 Hz, 2H), 2.651 (q, J=7.6 Hz, 2H), 1.245 (t, J=7.6 Hz, 3H). HR-FABMS Calcd for $C_{22}H_{21}N_3O_2$(M$^+$+H): 358.1556. Found: 358.1551.

Example 4

Synthesis of 4-chloro-N-(2-(4-ethylphenylamino)benzo[d]oxazol-5-yl)benzamide (4)

The title compound was prepared according to the same method as Example 2, except that p-chlorobenzoyl chloride was used in place of 2-phenylacetyl chloride used in Example 2.

White solid (40%), mp>250° C.; $^1$H NMR (CDCl$_3$, 400 MHz) δ 7.840 (d, J=8.8 Hz, 2H), 7.763 (s, 1H), 7.688 (d, J=1.6 Hz, 1H), 7.517-7.470 (m, 4H), 7.418 (d, J=8.4 Hz, 1H), 7.305 (d, J=8.4 Hz, 1H), 7.232 (d, J=8.0 Hz, 2H), 6.898 (brs, 1H), 2.651 (q, J=7.6 Hz, 2H), 1.244 (t, J=7.6 Hz, 3H). HR-FABMS Calcd for $C_{22}H_{19}ClN_3O_2$ (M$^+$+H): 392.1166. Found: 392.1161.

Example 5

Synthesis of 2-chloro-N-(2-(4-ethylphenylamino)benzo[d]oxazol-5-yl)-4-nitrobenzamide (5)

The title compound was prepared according to the same method as Example 2, except that 2-chloro-4-nitrobenzoyl chloride was used in place of 2-phenylacetyl chloride used in Example 2.

Yellow solid (35%), mp>250° C.; $^1$H NMR (Acetone-$d_6$, 400 MHz) δ 9.833 (s, 1H), 9.452 (s, 1H), 8.367 (s, 1H), 8.322 (d, J=8.2 Hz, 1H), 7.956 (d, J=8.4 Hz, 2H), 7.774 (d, J=8.4 Hz, 2H), 7.508 (d, J=8.8 Hz, 1H), 7.380 (d, J=8.4 Hz, 1H), 7.244 (d, J=8.4 Hz, 2H), 2.634 (q, J=7.6 Hz, 2H), 1.223 (t, J=7.6 Hz, 3H). HR-FABMS Calcd for $C_{22}H_{18}ClN_4O_4$ (M$^+$+H): 437.1017. Found: 437.1024.

Example 6

Synthesis of 2-chloro-N-(2-(4-ethylphenylamino)benzo[d]oxazol-5-yl)-5-nitrobenzamide (6)

The title compound was prepared according to the same method as Example 2, except that 2-chloro-5-nitrobenzoyl chloride was used in place of 2-phenylacetyl chloride used in Example 2.

White solid (35%), mp>250° C.; $^1$H NMR (Acetone-$d_6$, 400 MHz) δ 9.825 (s, 1H), 9.449 (s, 1H), 8.519 (s, 1H), 8.353 (dd, J=10.8 Hz, 1H), 7.974 (s, 1H), 7.857 (d, J=8.8 Hz, 1H), 7.773 (d, J=8.4 Hz, 2H), 7.504 (d, J=8.8 Hz, 1H), 7.381 (d, J=8.8 Hz, 1H), 7.244 (d, J=8.4 Hz, 2H), 2.634 (q, J=7.6 Hz, 2H), 1.223 (t, J=7.6 Hz, 3H). HR-FABMS Calcd for $C_{22}H_{18}ClN_4O_4$ (M$^+$+H): 437.1017. Found: 437.1011.

Example 7

Synthesis of 3,4-dichloro-N-(2-(4-ethylphenylamino)-benzo[d]oxazol-5-yl)benzamide (7)

The title compound was prepared according to the same method as Example 2, except that 3,4-dichlrobenzoyl chloride was used in place of 2-phenylacetyl chloride used in Example 2.

White solid (56%), mp>250° C.; $^1$H NMR (CDCl$_3$, 400 MHz) δ 7.999 (d, J=2.0 Hz, 1H), 7.742-7.698 (m, 2H), 7.585 (d, J=8.4 Hz, 1H), 7.506 (d, J=8.4 Hz, 2H), 7.390 (d, J=8.4 Hz, 1H), 7.308 (d, J=8.6 Hz, 1H), 7.234 (d, J=8.4 Hz, 2H), 6.902 (brs, 1H), 2.652 (q, J=7.6 Hz, 2H), 1.245 (t, J=7.6 Hz, 3H). HR-FABMS Calcd for $C_{22}H_{18}Cl_2N_3O_2$ (M$^+$+H): 426.0776. Found: 426.0768.

Example 8

Synthesis of 3-(chloromethyl)-N-(2-(4-ethylphenylamino)benzo[d]oxazol-5-yl)benzamide (8)

The title compound was prepared according to the same method as Example 2, except that 3-chlromethylbenzoyl chloride was used in place of 2-phenylacetyl chloride used in Example 2.

White solid (47%), mp 194.5-195° C.; $^1$H NMR (CDCl$_3$, 400 MHz) δ 7.924 (s, 1H), 7.832 (d, J=6.0 Hz, 1H), 7.713 (s, 1H), 7.594 (d, J=8.0 Hz, 1H), 7.526-7.488 (m, 3H), 7.421 (dd, J=8.8 Hz, 1H), 7.306 (d, J=8.4 Hz, 1H), 7.232 (d, J=8.4 Hz, 2H), 4.663 (s, 2H), 2.650 (q, J=7.6 Hz, 2H), 1.244 (t, J=7.6 Hz, 3H). HR-FABMS Calcd for $C_{23}H_{21}ClN_3O_2$ (M$^+$+H): 406.1322. Found: 406.1320.

Example 9

Synthesis of 4-ethyl-N-(2-(4-ethylphenylamino)benzo[d]oxazol-5-yl)benzamide (9)

The title compound was prepared according to the same method as Example 2, except that 4-ethylbenzoyl chloride was used in place of 2-phenylacetyl chloride used in Example 2.

White solid (60%), mp>250° C.; $^1$H NMR (Acetone-d$_6$, 400 MHz) δ 9.485 (s, 1H), 8.039 (d, J=2.0 Hz, 1H), 7.935 (d, J=7.2 Hz, 2H), 7.773 (d, J=6.8 Hz, 2H), 7.549 (dd, J=8.4 Hz, 1H), 7.363 (d, J=8.8 Hz, 2H), 7.332 (d, J=8.8 Hz, 1H), 7.240 (d, J=8.8 Hz, 2H), 2.725 (q, J=7.6 Hz, 2H), 2.632 (q, J=7.6 Hz, 2H), 1.273-1.182 (m, 6H). HR-FABMS Calcd for $C_{24}H_{24}N_3O_2$ (M$^+$+H): 386.1869. Found: 386.1867.

Example 10

Synthesis of N-(2-(4-ethylphenylamino)benzo[d]oxazol-5-yl)-3-fluoro-5-(trifluoromethyl)benzamide (10)

The title compound was prepared according to the same method as Example 2, except that 3-fluoro-5-(trifluoromethyl)benzoyl chloride was used in place of 2-phenylacetyl chloride used in Example 2.

White solid (77%), mp>250° C.; $^1$H NMR (Acetone-d$_6$, 400 MHz) δ 9.670 (s, 1H), 9.451 (s, 1H), 8.176 (d, J=6.0 Hz, 1H), 7.994-7.948 (m, 2H), 7.771 (d, J=6.4 Hz, 2H), 7.577-7.490 (m, 2H), 7.371 (d, J=8.8 Hz, 1H), 7.244 (d, J=8.8 Hz, 2H), 2.634 (q, J=7.6 Hz, 2H), 1.223 (t, J=7.6 Hz, 3H). HR-FABMS Calcd for $C_{23}H_{18}F_4N_3O_2$ (M$^+$+H): 444.1335. Found: 444.1333.

Example 11

Synthesis of 2-ethoxy-N-(2-(4-ethylphenylamino)-benzo[d]oxazol-5-yl)benzamide (11)

The title compound was prepared according to the same method as Example 2, except that 2-ethoxybenzoyl chloride was used in place of 2-phenylacetyl chloride used in Example 2.

White solid (75%), mp 181.6-182° C.; $^1$H NMR (Acetone-d$_6$, 400 MHz) δ 10.149 (s, 1H), 9.420 (s, 1H), 8.145 (dd, J=7.6 Hz, 1H), 8.020 (s, 1H), 7.537 (t, J=7.9 Hz, 1H), 7.473 (d, J=8.8 Hz, 1H), 7.255-7.212 (m, 2H), 7.127 (t, J=7.6 Hz, 1H), 4.381 (q, J=6.9 Hz, 2H), 2.636 (q, J=7.6 Hz, 2H), 1.654 (t, J=7.0 Hz, 3H), 1.226 (t, J=7.6 Hz, 3H). HR-FABMS Calcd for $C_{24}H_{24}N_3O_3$ (M$^+$+H): 402.1818. Found: 402.1815.

Example 12

Synthesis of 4-tert-butyl-N-(2-(4-ethylphenylamino)-benzo[d]oxazol-5-yl)benzamide (12)

The title compound was prepared according to the same method as Example 2, except that 4-t-butylbenzoyl chloride was used in place of 2-phenylacetyl chloride used in Example 2.

White solid (60%); $^1$H NMR (Acetone-d$_6$, 400 MHz) δ 9.468 (s, 1H), 9.395 (s, 1H), 8.043 (d, J=2.0 Hz, 1H), 7.942 (d, J=8.4 Hz, 2H), 7.774 (d, J=8.4 Hz, 2H), 7.579-7.538 (m, 3H), 7.334 (d, J=8.4 Hz, 1H), 7.240 (d, J=9.0 Hz, 2H), 2.633 (q, J=7.6 Hz, 2H), 1.364 (s, 9H), 1.224 (t, J=7.6 Hz, 3H). HR-FABMS Calcd for $C_{26}H_{28}N_3O_2$ (M$^+$+H): 414.2182. Found: 414.2186.

Example 13

Synthesis of N-(2-(4-ethylphenylamino)benzo[d]oxazol-5-yl)-3,4-dimethoxybenzamide (13)

The title compound was prepared according to the same method as Example 2, except that 3,4-dimethoxybenzoyl chloride was used in place of 2-phenylacetyl chloride used in Example 2.

White solid (75%), mp>250° C.; $^1$H NMR (Acetone-d$_6$, 400 MHz) δ 9.417 (s, 1H), 9.386 (s, 1H), 8.014 (d, J=2.4 Hz, 1H), 7.771 (d, J=8.4 Hz, 2H), 7.635 (dd, J=8.4 Hz, 1H), 7.607 (s, 1H), 7.497 (dd, J=8.6 Hz, 1H), 7.323 (d, J=8.8 Hz, 1H), 7.239 (d, J=8.4 Hz, 2H), 7.058 (d, J=8.4 Hz, 1H), 3.894 (s, 3H), 2.774 (s, 3H), 2.633 (q, J=7.6 Hz, 2H), 1.224 (t, J=7.6 Hz, 3H). HR-FABMS Calcd for $C_{24}H_{24}N_3O_4$ (M$^+$+H): 418.1767. Found: 418.1771.

Example 14

Synthesis of N-(2-(4-ethylphenylamino)benzo[d]oxazol-5-yl)-3,4,5-trimethoxybenzamide (14)

The title compound was prepared according to the same method as Example 2, except that 3,4,5-trimethoxybenzoyl chloride was used in place of 2-phenylacetyl chloride used in Example 2.

White solid (66%), mp>250° C.; $^1$H NMR (Acetone-d$_6$, 400 MHz) δ 9.470 (s, 1H), 9.400 (s, 1H), 7.984 (d, J=2.0 Hz, 1H), 7.772 (d, J=8.4 Hz, 2H), 7.454 (dd, J=8.6 Hz, 1H), 7.342-7.321 (m, 3H), 7.241 (d, J=8.4 Hz, 2H), 3.912 (s, 3H), 3.800 (s, 3H), 2.776 (s, 3H), 2.634 (q, J=7.6 Hz, 2H), 1.224 (t, J=7.6 Hz, 3H). HR-FABMS Calcd for $C_{25}H_{26}N_3O_5$ (M$^+$+H): 448.1872. Found: 448.1868.

Example 15

Synthesis of N-(2-(4-ethylphenylamino)benzo[d]oxazol-5-yl)-4-heptylbenzamide (15)

The title compound was prepared according to the same method as Example 2, except that 4-heptylbenzoyl chloride was used in place of 2-phenylacetyl chloride used in Example 2.

Pale brown solid (73%), mp 244.8-246° C.; $^1$H NMR (Acetone-d$_6$, 400 MHz) δ 9.472 (s, 1H), 9.391 (s, 1H), 8.043 (d, J=2.4 Hz, 1H), 7.929 (d, J=8.0 Hz, 2H), 7.774 (d, J=8.8 Hz, 2H), 7.550 (dd, J=8.8 Hz, 1H), 7.364-7.322 (m, 3H), 7.240 (d, J=8.8 Hz, 2H), 2.704 (t, J=7.6 Hz, 2H), 2.633 (q, J=7.6 Hz, 2H), 1.684-1.647 (m, 2H), 1.366-1.293 (m, 8H), 1.224 (t, J=7.6 Hz, 3H), 0.886 (t, J=7.6 Hz, 3H). HR-FABMS Calcd for $C_{29}H_{34}N_3O_2$ ($M^+$+H): 456.2651. Found: 456.2657.

Example 16

Synthesis of N-(2-(4-ethylphenylamino)benzo[d]oxazol-5-yl)-2-(3-(trifluoromethyl)phenylamino)benzamide The title compound was prepared according to the same method as Example 2, except that 2-(3-(trifluoromethyl)phenylamino)-benzoic acid was used in place of 2-phenylacetyl chloride used in Example 2.

Pale brown solid (38%), mp 174-176° C.; $^1$H NMR (Acetone-$d_6$, 400 MHz)_9.706 (s, 1H), 9.511 (s, 1H), 9.417 (s, 1H), 7.971-7.959 (m, 1H), 7.862 (d, J=7.6 Hz, 1H), 7.781-7.743 (m, 2H), 7.539-7.435 (m, 5H), 7.374-7.339 (m. 1H), 7.261-7.218 (m, 3H), 7.005 (t, J=7.2 Hz, 1H), 2.632 (q, J=7.6 Hz, 2H), 1.222 (t, J=7.6 Hz, 3H). HR-FABMS Calcd for $C_{29}H_{24}F_3N_4O_2$ ($M^+$+H): 517.1851. Found: 517.1854.

B. Efficacy Test

Experiment 1

In Vitro Identification of Effect of the Compound of the Present Invention (1) Preparation of pSTAT3-TA-Luc6 Construct A pSTAT3-TA-Luc6 construct, which comprises 8 more STAT3 DNA binding sequence copies as compared to pSTAT-3-TA-Luc and thus, enables to better reflect STAT3 reporter gene assay, was prepared. STAT3 DNA binding sequence was amplified using pSTAT3-TA-Luc plasmid (Clontech, Palo Alto, Calif.) as the template, and oligonucleotide (AGAGGG-TAACGGTACCGTGCTTCCCGAACGTTGCTTCC. SEQ ID NO: 1 (containing Kpn I site)) and oligonucleotide (GTACGCAAGGCTCGAGCTACGTTCGG GAAG-CAACGTTC (containing Xho I site)) as forward primer and reverse primer, respectively, by means of a thermocycler. The amplified PCR product was cloned, separated, and then inserted into Kpn I/Xho I site of pSTAT3-TA-Luc plasmid.

(2) IL-6 Reactive STAT3 Reporter Gene Test

Human hepatoma cell line, HepG2 cell, was incubated in MEM (Minimal Essential Medium, WelGENE Inc, Daegu, Korea) medium under water-saturated condition at 37° C., 5% $CO_2$. To this medium was added 10% (v/v) fetal bovine serum, streptomycin (100 U/mL) and penicillin (100 U/mL). 6-Well cell culture plate was allowed to grow cells up to 80%, and then the specimen was pre-treated for one hour. Then, the medium was changed into 50 μL of serum-free medium, and the mixed solution of 0.1 μL pSTAT3-TA-Luc6 construct and 0.3 μL lipofectamin reagent was added to each well and then allowed to react for 3 hours to transfect cells with pSTAT3-TA-Luc6 construct. The medium was changed to a fresh medium, and the plate was incubated for 24 hours to transiently transfect cells. The transfected cells were serum-starved with 1% BSA/DMEM, and treated with the samples for one hour and then, after adding IL-6, incubated for 3 hours. The mixture was washed with PBS, shaken for one minute with addition of 50 μL of lysis buffer (promega luciferase assay system). After adding 30-100 μL of luciferase substrate (Promega luciferase assay system), the mixture was measured by a luminometer within 5 minutes.

To identify the inhibition degree against the activity of IL-6 reactive STAT3 reporter gene, the inhibitory effect exhibited in STAT3 reporter gene when treated with 20 ug/ml of respective synthesized samples is shown together with the structures of benzoxazole derivatives used in the test (Table 2). The synthesized materials exhibited various inhibitory activities in the range of 12-97% depending on the kinds of substituents in amino group with Compound 1 as the material having the substituent H showing the highest inhibitory effect of 97%. In addition, Compounds 3, 8, 12, 14, and 16 showed high inhibitory effect above 80%.

TABLE 2

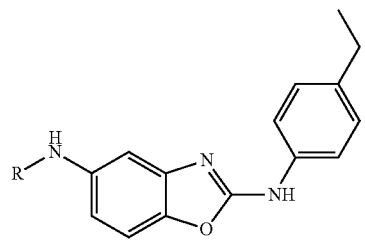

| Compound | R | Inhibition % |
|---|---|---|
| 1 | H | 97.5 |
| 2 | (benzyl-C(=O)-) | 61.7 |
| 3 | (phenyl-C(=O)-) | 93.1 |
| 4 | (4-Cl-phenyl-C(=O)-) | 12.1 |
| 5 | (4-O₂N-2-Cl-phenyl-C(=O)-) | 20.0 |
| 6 | (5-NO₂-2-Cl-phenyl-C(=O)-) | 65.6 |

TABLE 2-continued

[Structure: R-NH-benzoxazole-NH-(4-ethylphenyl)]

| Compound | R | Inhibition % |
|---|---|---|
| 7 | 3,4-dichlorobenzoyl | 69.3 |
| 8 | 3-(chloromethyl)benzoyl | 91.7 |
| 9 | 4-ethylbenzoyl | 63.3 |
| 10 | 3-fluoro-5-(trifluoromethyl)benzoyl | 50.2 |
| 11 | 2-ethoxybenzoyl | 58.0 |
| 12 | 4-tert-butylbenzoyl | 86.5 |
| 13 | 3,4-dimethoxybenzoyl | 26.2 |
| 14 | 3,4,5-trimethoxybenzoyl | 83.7 |
| 15 | 4-(H$_3$C(H$_2$C)$_6$)benzoyl | 57.2 |
| 16 | 2-((3-trifluoromethylphenyl)amino)benzoyl | 84.6 |

Figure 2:
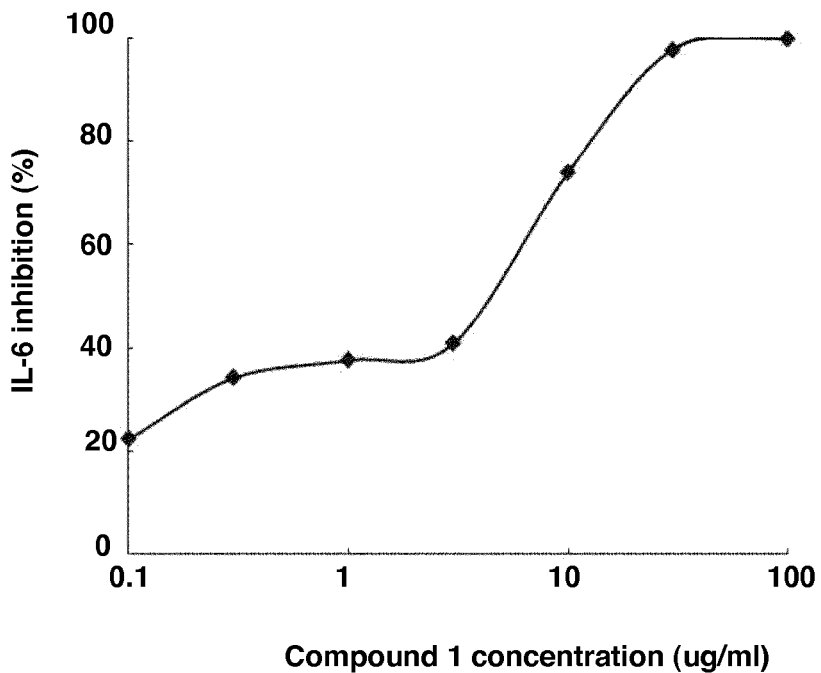
FIG. 2 is a graph showing the IL-6 inhibitory activity of Compound 1 at various concentrations.
Figure 3:
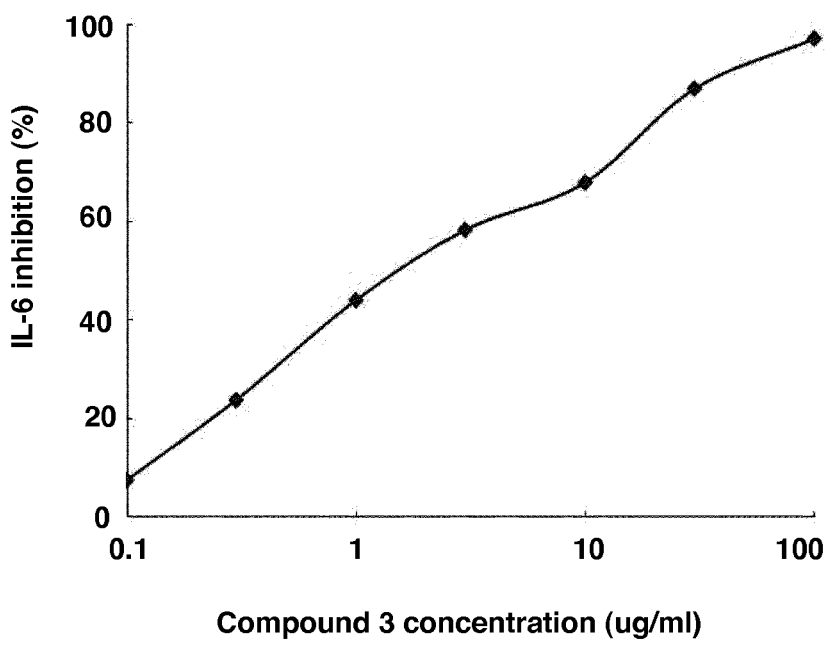
FIG. 3 is a graph showing the IL-6 inhibitory activity of Compound 3 at various concentrations.

Among others Compounds 1 and 3 as the materials having high inhibitory effect on IL-6 activity were used at various concentration to measure the degree of inhibitory effect, and the results thereof are as shown in FIGS. 2 and 3. The IC$_{50}$ values of Compounds 1 and 3 were 18.9 μM and 5.8 μM, respectively.

(3) Test for Inhibitory Activity Against STST3 Phosphorylation Induced by IL-6

HepG2 cells were divisionally inoculated in 6-well plate in the ratio of 5×10$^4$ cells/well, and grown to be 80% confluent. After changing to a serum-free medium and incubating for 6 hours, cells were pre-treated with the samples for one hour. Then, they were treated with 20 ng/ml IL-6, and after reacting for 10 minutes, cells were lysed with a lysis buffer (20 mM Tris-HCl, pH 8, 137 mM NaCl, 10% glycerol, 1% Triton X-100, 1 mM Na$_3$VO$_4$, 2 mM EDTA, 1 mM PMSF, 20 mM leupeptin, 20 mg/ml aprotonin). Then the mixture was centrifuged (13,000×g, 15 minutes) to obtain a lysate as the supernatant. Herein, HepG2 cells not treated with IL-6 and the samples were used as the control group. The concentration of proteins was quantified by means of Bio-Rad DC protein assay kit, and the protein was loaded on 10% SDS-polyacrylamide gel (SDS-PAGE) and electrophoresed at 30 mA for 2 hours. After completion of the electrophoresis, the protein on gel was transcribed into PVDF membrane (Westran® S, pore size 0.2 mm) at 90V for 90 minutes, and the transcribed membrane was blocked with Tris-buffered solution (T-TBS; 50 mM Tri-HCl, pH 7.6, 150 mM NaCl, 0.2% Tween-20, 5% skim milk) at 4° C. for 12 hours, and washed five time with T-TBS. The membrane was treated with polyclonal antibodies of phospho-STAT3 (1:1000 dilutions, respectively) as the primary antibody for 2 hours. After washing five times with T-TBS, the membrane was reacted with HRP-conjugated anti-rabbit antibody (1:5000 dilutions) as the secondary antibody for one hour. After washing with T-TBS, the film was developed in the dark room by means of ECL.

Figure 4:
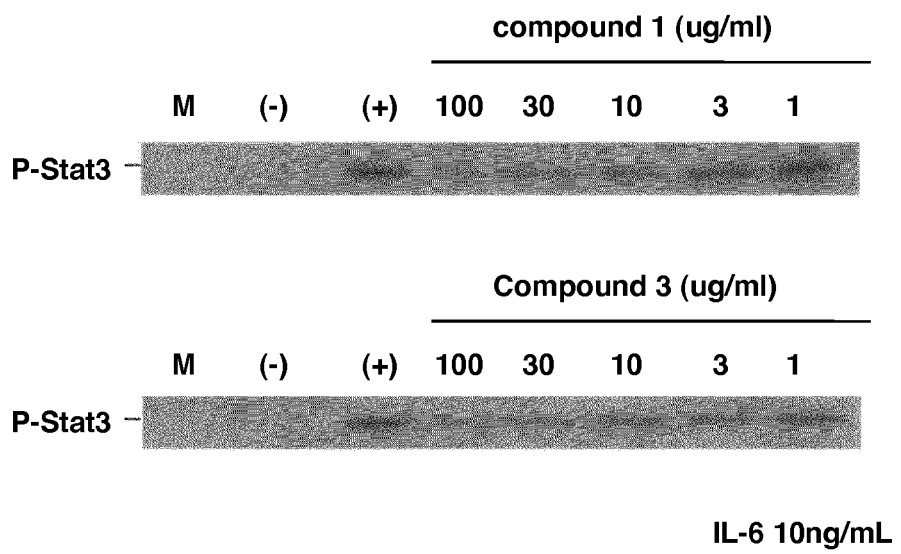
FIG. 4 is a drawing showing the activity of Compounds 1 and 3 on STAT3 expression.

To test the inhibitory activity of Compounds 1 and 3 samples, which exhibited high inhibitory activity in IL-6 reactive STAT3 reporter gene test, on IL-6 induced STST3 phosphorylation in cell lines, cells were treated with the samples at the concentration of 1, 3, 10, 30, 100 ug/ml, ad then treated with 10 ng/ml of IL-6 to test the inhibitory activity on IL-6 expression. The result thereof showed that Compounds 1 and 3 inhibited IL-6 expression in a concentration-dependent manner (FIG. 4).

(4) Test for Inhibitory Activity Against ERK Phosphorylation Induced by IL-6

HepG2 cell was divisionally inoculated in 6-well plate, and then starved for 18 hours.

The starved cells were treated with the samples for one hour, and then stimulated with IL-6 or LIF (Upstate Biotechnology, USA) for 10 minutes. The specimen was treated with 5× cell lysis buffer (Promega) sometimes with vortexing under ice for 30 minutes. The cell lysate obtained as described under B in Experiment 1 (3) was dissolved in 8% SDS-PAGE gel, and transferred to the nitrocellulose membrane. This membrane was blocked with Tris-buffered solution (50 mM Tris-HCl (pH 7.4), 150 mM NaCl, 0.1% Tween 20) containing 5% non-fat dry milk at 4° C. Then, it was incubated together with an appropriate primary antibody (ERK) present in Tris-buffered solution (50 mM Tris-HCl (pH 7.4), 150 mM NaCl, 0.1% Tween 20) containing 5% non-fat dry milk, at room temperature for 1-2 hours. This membrane was washed five times with TBS buffer solution for 10 minutes, and incubated with 1:6000 diluted horseradish peroxidase-conjugated secondary antibodies for one hour. The membrane was washed 10 times with TBS buffer solution, and then mixed and incubated with the 1:1 mixture of HRP Substrate Luminol Reagent and HRP Substrate Peroxide Solution as ELC reagent (Millipore Corp. Ma USA). The chemiluminescent signals were visualized with X-ray film.

Figure 5:
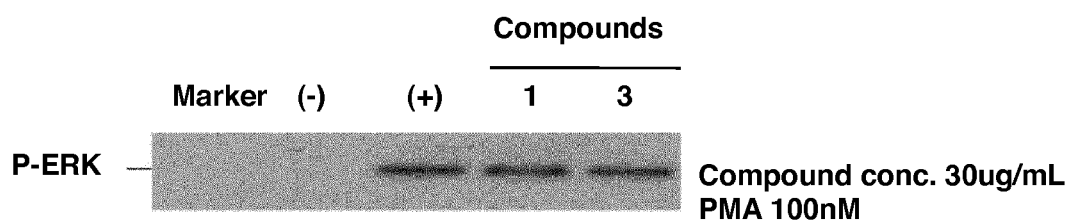
FIG. 5 is a drawing showing the activity of Compounds 1 and 3 on ERK expression.

The results of the test of the inhibitory activity of Compounds 1 and 3 samples, which exhibited high inhibitory activity in IL-6 reactive STAT3 reporter gene test, on IL-6 induced STST3 phosphorylation in cell lines are as shown in FIG. 5. That is, although it was shown that Compounds 1 and 3 inhibited IL-6 expression in a concentration-dependent manner, treatment with 30 μg/ml of Compounds 1 and 3 did not influence on ERK phosphorylation (FIG. 5).

(5) Cytotoxicity Assay

In testing the compounds in cell lines, if cells are killed due to a toxicity of the compounds at the treatment concentration, a significant result cannot be obtained. Therefore, the toxicity assay was conducted by treatment with the compounds as follows. Respective cell lines were maintained on 96-well cell culture plate in the medium comprising 10% FBS with 1% Penicillin G/streptomycin, and then incubated under 37° C., 5% $CO_2$ condition. All the experiments were repeated three times. The samples were properly diluted, and then cells were treated with the diluted samples at the concentrations of 1, 3, 10, 30, 100 μg/ml. After 48 hours, 10% (v/v) 5 mg/mL 3-(4,5-dimethylthiazol-2-yl)-2,5-diphenyltetrazolium bromide (MTT; Sigma) was added to the cell culture. After 3 hours of the incubation, the medium was aspirated and washed with PBS. After adding DMSO (100 μl), the mixture was gently agitated for 5 minutes. The absorbance was measured at 570 nm by means of VERSA max microplate reader (Molecular Devices Inc.), and the average absorbance (±SE) values as obtained from three experiments were compared with t-test, a statistical significance of $P<0.05$. When Compounds 1 and 3 were used at the concentrations of 1, 3, 10, 30, 100 μg/ml, the survival rates of cells were 94, 76, 70, 67, 30%, respectively, by the treatment with Compound 1, and 74, 71, 65, 57, 19%, respectively, by the treatment with Compound 3. It means that at least 50% of cells survive at the concentration (for example, 30 μg/ml) of the compounds of the present invention for measuring IL-6 inhibitory activity.

Experiment 2

Figure 6:
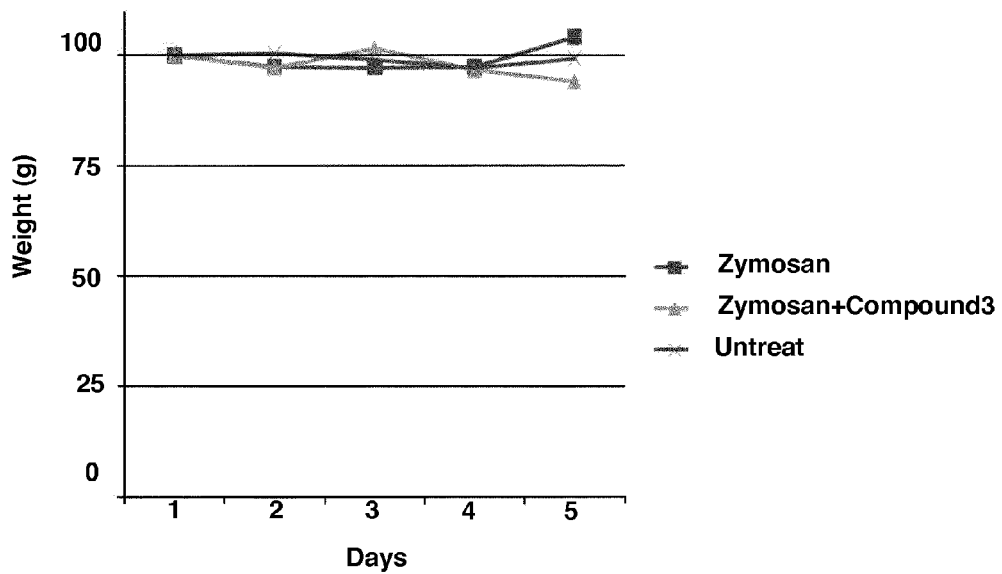
FIG. 6 is a graph showing a change in weight of the test animal with Compound 3 treatment.

In Vivo Identification of Effect of the Compound of the Present Invention (1) Test of a Toxicity of the Compounds In the animal experiments, C57BL/6 female mice (control group 4 mice, test group (dose group) 4 mice) obtained from Central Lab. Animal Inc. were used. The experimental animals were acclimated by breeding them at the place established with temperature 23 ±3° C., relative humidity 50 ±10%, lighting time 12 hours (6 a.m.-6 p.m.), number of ventilation 10-20 times/hour, and illuminance 150-300 Lux, for one week. All the testers who evaluated the activity in animals worn high-pressure steam sterilized (121° C., 20 minutes) working clothes, hood, mask and gloves, and conducted the experiment. During the periods of accommodation and quarantine the experimental animals were accommodated in a polycarbonate-made shoes box-type breeding cage (260W×410L×200H mm) by 4 mice in each cage. During the periods of administration and observation, the experimental animals were accommodated in a wire breeding cage (205W× 350 L×175H mm) with one mouse in each cage. During the period of experiments, the breeding cages were discriminated with attaching the labels in which the experiment numbers and the animal numbers were entered. The animals were allowed to freely ingest a radiation-sterilized (25 kGy, Picolab) solid feed for experimental animals as the feed, and tap water, which was sterilized with an autoclave, as the drinking water by means of a water bottle. In the control group, Zymosan A (Sigma-Aldrich, St. Louis, Mo., USA) separated from *Saccharomyces cereviciae* was prepared as 3 mg/ml concentration and then intraperitoneally injected at a dose of 50 μl, and 3 mg/kg of Compound 3 was intraperitoneally administered once a day, i.e. at 4 p.m. every day, to practice the experiments for 5 days. When measuring the body weight on Days 1, 3, 4, 5, a change in weigh of the experimental animals was substantially not observed. In addition, as the result of comparison between the weights in the control group and the Compound 3-treated group (30 mg/kg) at the interval of one day, it could be identified that the Compound 3-treated group did not show any change in the weight as compared to the control group. Furthermore, after 6 days at which the experiment was completed, the experimental animals did not show any toxic symptom in appearance (FIG. 6, Change in weight of the test animal with Compound 3 treatment).

(2) Effect of Alleviating the Compound 3-Induced Inflammation

Among the candidate materials having a superior inhibitory activity on STAT3 binding as measured in vitro, Compound 3 was evaluated in vivo for the activity to alleviate the inflammation.

Figure 7:
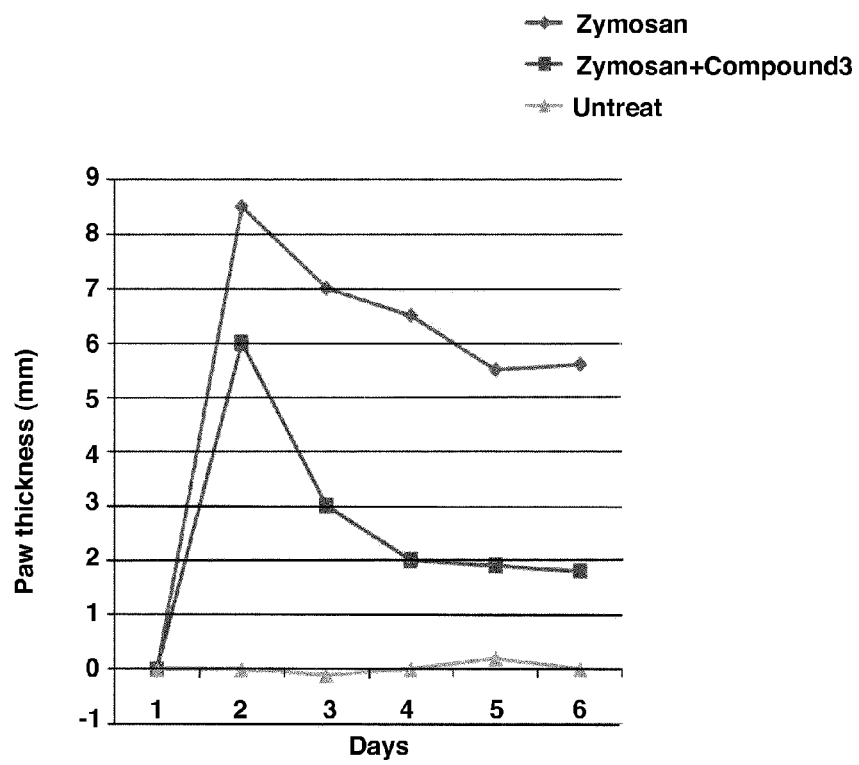
FIG. 7 is a graph showing a change in the alleviation of inflammation with Compound 3 treatment.

For this experiment, C57BL/6 mice were obtained from Central Lab. Animal Inc., and acclimated for one week and then used in the experiment. The gender of animals used in the experiment was female, and 4 mice were used in each of the control group and the test group (Doe group). To experiment Compound 3's effect of alleviating the inflammation, the thicknesses of paws having the inflammation is reduced by injecting 3 mg of Zymosan A and 30 mg/kg of Compound 3 into right paws of the experimental animals, and both the paw thicknesses in the control group to which Zymosan A was administered to induce the inflammation and the control group having no treatment were measured every day, and the results are as shown in FIG. 7.

Figure 8:
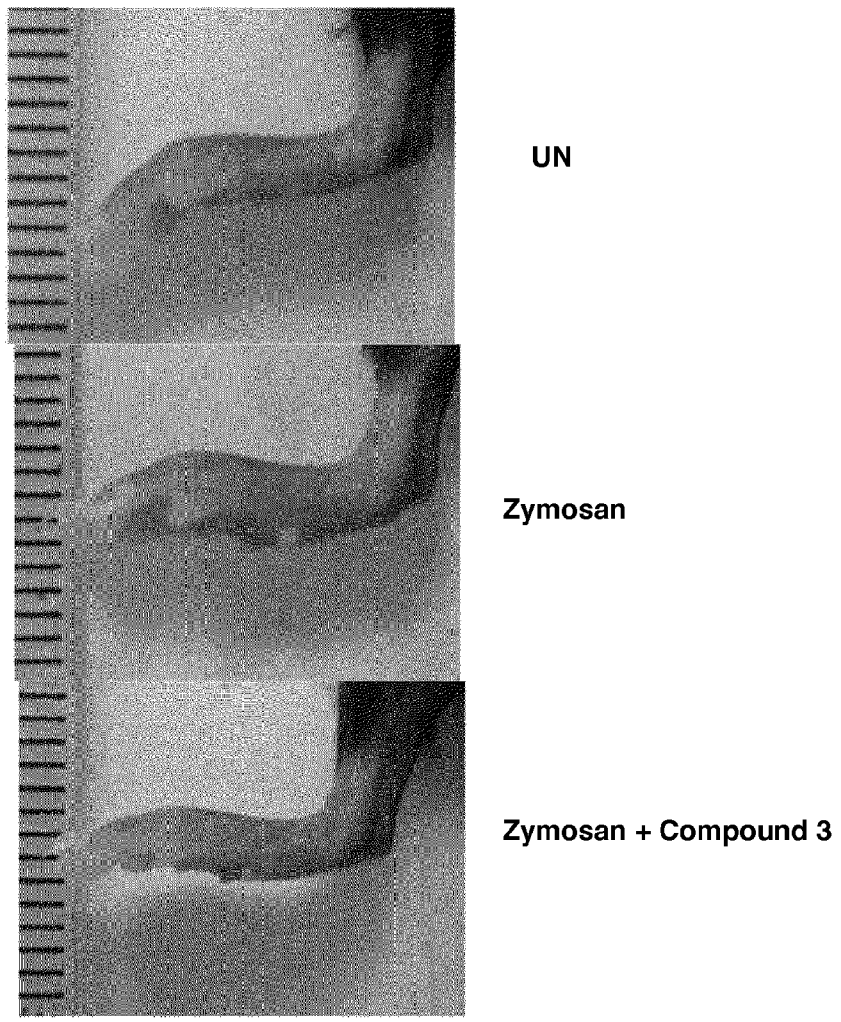
FIG. 8 is a photograph of a mouse paw demonstrating the alleviation of inflammation with Compound 3 treatment.

When a difference between the thicknesses of the right paw and left paw of the test group in which the inflammation was alleviated by Zymosan A and Compound 3 was measured on the basis of a difference between the thicknesses of the right paw and left paw of the test group in which the inflammation was induced by Zymosan A, it could be identified that treatment with Compound 3 exhibited the effect of alleviating the inflammation. When the paw thickness was measured every day after inducing the inflammatory reaction by Zymosan, a difference between the thicknesses of the right paw and left paw was 8.5, 7.0, 6.5, 5.5, 5.6 mm. It could be identified that by treatment with Zymosan and Compound 3 the inflammatory reaction was alleviated so that a difference between paw thicknesses was 6.0, 3.0, 2.0, 1.9, 1.8 mm. A difference between paw thicknesses could also be identified in real photographs of the group treated only with Zymosan, the test group treated with Zymosan and Compound 3, and the control group having no treatment of the experimental animals on the $6^{th}$ day in the inflammation alleviating assay (FIG. 8).

What is claimed is:

1. A compound having the chemical structure of Formula 1:

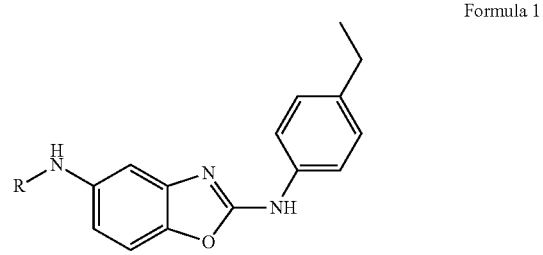

Formula 1 or a pharmaceutically acceptable salt thereof, wherein

R is hydrogen, $R_1CH_2CO$ or $R_1CO$;

$R_1$ is phenyl which is unsubstituted or substituted with one to three identical or different substituents each independently selected from the group consisting of $C_{1-10}$ alkyl, halogen, nitro, $C_{1-4}$ haloalkyl, $C_{1-4}$ alkoxy, and and $R_2$ is $C_{1-4}$ haloalkyl.

2. The compound according to claim 1 characterized in that said $R_1$ is phenyl substituted with one of $C_{1-10}$ alkyl, $C_{1-4}$ haloalkyl, halogen, and

SEQUENCE LISTING

<160> NUMBER OF SEQ ID NOS: 2

<210> SEQ ID NO 1
<211> LENGTH: 38
<212> TYPE: DNA
<213> ORGANISM: Artificial Sequence
<220> FEATURE:
<223> OTHER INFORMATION: forward primer for STAT3 DNA binding sequence
      PCR

<400> SEQUENCE: 1
agagggtaac ggtaccgtgc ttcccgaacg ttgcttcc                         38

<210> SEQ ID NO 2
<211> LENGTH: 38
<212> TYPE: DNA
<213> ORGANISM: Artificial Sequence
<220> FEATURE:
<223> OTHER INFORMATION: reverse primer for STAT3 DNA binding sequence
      PCR

<400> SEQUENCE: 2
gtacgcaagg ctcgagctac gttcgggaag caacgttc                         38

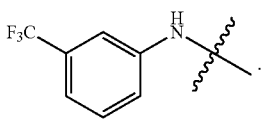

3. The compound according to claim 1 characterized in that said $R_1$ is phenyl substituted with two identical or different substitutents each independently selected from the group consisting of halogen, nitro, $C_{1-4}$ haloalkyl and $C_{1-4}$ alkoxy.

4. The compound according to claim 3 characterized in that said $R_1$ is phenyl substituted with a halogen and a nitro, phenyl substituted with a halogen and a $C_{1-4}$ haloalkyl, phenyl substituted with two halogens, or phenyl substituted with two $C_{1-4}$ alkoxy.

5. The compound according to claim 1 characterized in that said $R_1$ is phenyl substituted with three $C_{1-4}$ alkoxy.

6. The compound according to claim 1 characterized in that said $R_1$ is phenyl which is unsubstituted or substituted with one to three identical or different substituents, each independently selected from the group consisting of ethyl; t-butyl; heptyl; chloromethyl; trifluoromethyl; fluoro; chloro; nitro; methoxy; ethoxy; and

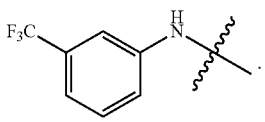

7. The compound according to claim 1 characterized in that said $R_2$ is trifluoromethyl.

8. The compound according to claim 1 characterized in that the compound is selected from the group consisting of:
   N-(2-(4-ethylphenyl)benzo[d]oxazole-2,5-diamine,
   N-(2-(4-ethylphenylamino)benzo[d]oxazol-5-yl)-2-phenylacetamide,
   N-(2-(4-ethylphenylamino)benzo[d]oxazol-5-yl)benzamide,
   4-chloro-N-(2-(4-ethylphenylamino)benzo[d]oxazol-5-yl)benzamide,
   2-chloro-N-(2-(4-ethylphenylamino)benzo[d]oxazol-5-yl)-4-nitrobenzamide,
   2-chloro-N-(2-(4-ethylphenylamino)benzo[d]oxazol-5-yl)-5-nitrobenzamide,
   3,4-dichlorobenzamide-N-(2-(4-ethylphenylamino)benzo[d]oxazol-5-yl)benz amide,
   3-(chloromethyl)-N-(2-(4-ethylphenylamino)benzo[d]oxazol-5-yl)benzamide,
   4-ethyl-N-(2-(4-ethylphenylamino)benzo[d]oxazol-5-yl)benzamide,
   N-(2-(4-ethylphenylamino)benzo[d]oxazol-5-yl)-3-fluoro-5-(trifluoromethyl)benz amide,
   2-ethoxy-N-(2-(4-ethylphenylamino)benzo[d]oxazol-5-yl)benzamide,
   4-t-butyl-N-(2-(4-ethylphenylamino)benzo[d]oxazole-5-yl)benzamide,
   N-(2-(4-ethylphenylamino)benzo[d]oxazol-5-yl)-3,4-dimethoxybenzamide,
   N-(2-(4-ethylphenylamino)benzo[d]oxazol-5-yl)-3,4,5-trimethoxybenzamide,
   N-(2-(4-ethylphenylamino)benzo[d]oxazol-5-yl)-4-heptylbenzamide, and
   N-(2-(4-ethylphenylamino)benzo[d]oxazol-5-yl)-2-(3-(trifluoromethyl)phenyl amino)benzamide.

9. A pharmaceutical composition comprising the compound according to claim 1 and a pharmaceutically acceptable carrier or a pharmaceutically acceptable salt thereof.

10. The pharmaceutical composition according to claim 9, wherein said compound is effective to treat an inflammation.

11. A method for preparing a compound having the chemical structure of Formula 1:

Formula 1

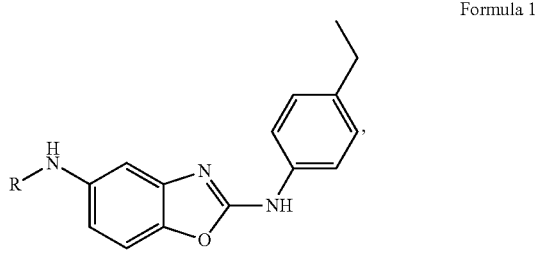

comprising the step of:
reacting a compound having the chemical structure of Formula 2:

Formula 2

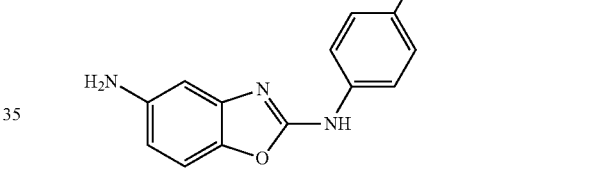

with a compound having the chemical structure of Formula 3:

R—X    Formula 3 in the presence of a base, wherein R is $R_1CH_2CO$ or $R_1CO$ and $R_1$ is phenyl which is unsubstituted or substituted with one to three identical or different substituents each independently selected from the group consisting of $C_{1-10}$ alkyl, halogen, nitro, $C_{1-4}$ haloalkyl, $C_{1-4}$ alkoxy, and

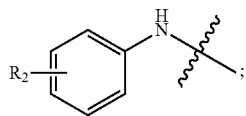

and
$R_2$ is C1-4 haloalkyl.

12. The method according to claim 11 characterized in that said base is selected from the group consisting of triethylamine, N,N-diisopropylethylamine, N-methylmorpholine, N-methylpiperidine, 4-dimethylaminopyridine, N,N-dimethylaniline, 2,6-lutidine and pyridine.

13. The method according to claim 11 characterized in that the equivalent ratio of the compound of Formula 2 and the compound of Formula 3 is 1:0.9 to 1.5.

* * * * *